United States Patent [19]

Kim

[11] Patent Number: 4,528,192

[45] Date of Patent: Jul. 9, 1985

[54] PROCESS FOR PREPARING AN ANTITOXIC COMPOSITION

[76] Inventor: Jong Seong Kim, 508-2 Wolgye-dong, Seongbuk-Ku, Seoul, Rep. of Korea, 131

[21] Appl. No.: 643,096

[22] Filed: Aug. 22, 1984

Related U.S. Application Data

[63] Continuation of Ser. No. 341,495, Jan. 21, 1982, abandoned.

[51] Int. Cl.³ ............................................. A61K 35/78
[52] U.S. Cl. .................................................. 424/195.1
[58] Field of Search ......................................... 424/195

[56] References Cited

U.S. PATENT DOCUMENTS 3,694,549  9/1972  Livingston .......................... 424/147

*Primary Examiner*—Albert T. Meyers
*Assistant Examiner*—John W. Rollins
*Attorney, Agent, or Firm*—Holman & Stern

[57] ABSTRACT

An antitoxic galenical composition consisting of an extract of various medicinal herbs and glycerin is provided. This composition is useful in expelling in a short period of time toxic ingredients from the animal body poisoned by toxic materials.

2 Claims, No Drawings

PROCESS FOR PREPARING AN ANTITOXIC COMPOSITION

This is a continuation of application Ser. No. 341,495, filed Jan. 21, 1982 now abandoned.

This invention relates to an antitoxic composition for animals and a process for preparing the composition. More particularly, this invention relates to with a veterinary antitoxic general composition consisting of medicinal herb extracts.

Recently, there has been a progressively increase in the number of animals including cattle and birds injured due to toxicity from various agricultural chemicals; the ecological environment is being destroyed and animal resources are in a state of disorder. Hitherto, there have been proposed no fundamental measures to prevent and to remedy those injuries.

Therefore, the essential object of the invention is to provide an antitoxic composition which can immediately remedy such toxicity due to chemicals.

This object can be achieved by the process according to the invention which comprises uniformly admixing a blend of 70 wt.% of cut dry leaf or bark of oak tree (*Quercus spp.*), 20 wt.% of cut dry leaf or root of juniper tree (*Juniperus utilis*), 5 wt.% of cut dry root of arrowroot (*Pueraria Thunber giana*) and 2.5 wt.% of licorice root (*Glycyrrhiza uralensis*) with water in a weight ratio of 1:3; cooking the first resulting mixture for 5 to 6 hours at a temperature of 40° to 60° C.; extracting the resulting cooked mixture under reduced pressure to get a first extract; admixing said first extract with said first mixture in a weight ratio of 3:1; boiling in vacuum the second resulting mixture for 0.5 to 1.0 hour at 110° C. and then extracting said mixture to obtain a second extract; boiling in vacuum said extract for 5 to 6 hours at 110° C. to afford a third extract; and dispersing 0.5 wt.% of glycerin into said extract at a high speed.

In the field of Chinese herb medicines, leaf or bark of oak tree is used as an astringent or mordant, and leaf or root of juniper tree as a diuretic, incense making or anticonvulsive. Orange peel contains limonene and hesperidion (a kind of glycoside), and is used as an aromatic stomach tonic, digestive, or expectorant. The arrowroot contains diadzin with its decomposition products, diadzein and puerarian, and therefore it has been used as an anticonvulsive or expellent, or antifebric for curing tonsillitis and conjunctivitis. The licorice root contains a kind of saponin consisting mainly of glycyrribizin, and is used as an expectorant, corrective, expellent, or sweetening. Glycerin is, as well known, used as a general solvent or carrier for the preparation of softening agents, clysters or suppositories; it is dispersed into the composition of the invention at about 800–1000 rpm.

When the antitoxic composition according to the invention is preferably administered orally or nasally to an animal poisoned by an agricultural chemical such as pesticides, i.e. BPMC, Dimercron or DDVP emulsion, the composition is absorbed in the body of the animal at every inhalation of its breath. Thus, the animal can be recovered immediately or progressively depending upon the extent of toxic effect and moreover, the residual toxic character can be removed. The pharmacological or biochemical mechanism of this antitoxic action has not yet been proved. It is presumed that the composition of the invention probably can act as a strong promoter for an oxygen-transfer reaction and has a relation with the biochemical reaction to expel toxic materials from a living body.

The composition of the invention can be in any of the preparation forms which are usually employed in the field of pharmaceutical techniques; however it is useful to form the composition as a liquid preparation suitable for oral or nasal administration. The unit dosage can be increased or decreased depending upon the extent of poisoning.

The following examples are illustrative of the invention and constitute preferred embodiments.

EXAMPLE 1

Preparation of an antitoxic galenical composition (I).

A mixture (hereinafter, "mixture A") was prepared by uniformly admixing 70 g of cut oak tree leaf ("KL") 20 g of cut juniper tree leaf ("JL") 5 g of cut orange peel ("GI"), 2.5 g of cut arrowroot ("CH") and 2.5 g of cut licorice root ("KA"). The mixture A was added to 300 ml of water in a jar, and warmed gently at 50° C. for 5 hours with stirring. The warmed solution was extracted. A mixture of 300 ml of this extract and 100 g of the mixture A separately prepared was boiled in vacuum at 110° C. for 0.5 hour and then extracted again. The resulting extract was boiled in vacuum at 110° C. for 4 hours while condensing with a condenser. The condensed product was admixed with 0.5 wt.% of glycerin at a high speed.

EXAMPLE 2

Preparation of an antitoxic galenical composition (II).

Substituting oak free leaf and juniper tree leaf with 70 g of oak tree bark ("KP") and 20 g of juniper tree root ("JP"), the whole procedure of Example 1 was repeated.

With the antitoxic compositions I and II obtained in Examples 1 and 2, the following tests were conducted.

As test animals, mudfishes were used. These mudfishes were knock-down by poisoning with a diluted solution of Dimecron in water (1:1000) and then, each of the compositions of Examples 1 and 2 was added thereto in a small quantity. The effect of each composition was investigated.

TABLE I

| Ingredient | Ingredient Tested Amount (drop)[1] | Time (sec.)[2] | Effect (%)[3] |
|---|---|---|---|
| KL | 8 | 2 | 60 |
| KP | 8 | 2 | 60 |
| JI | 15 | 2 | 30 |
| JP | 15 | 5 | 30 |
| GI | 12 | 7 | 20 |
| CH | 10 | 5 | 40 |
| KA | 10 | 5 | 40 |
| KA + JL | 8 | 2 | 65 |
| KL + GI | 8 | 2 | 60 |
| KL + CH | 8 | 2 | 65 |
| KL + KA | 8 | 2 | 65 |
| JL + GI | 15 | 5 | 40 |
| JL + CH | 10 | 5 | 45 |
| JL + KA | 10 | 5 | 45 |
| GI + CH | 15 | 5 | 40 |
| GI + KA | 15 | 5 | 40 |
| CH + KA | 10 | 5 | 45 |
| Water | 20 | — | — |
| I | 8 | 2 | 95 |
| II | 8 | 2 | 95 |

[1] One drop corresponds to an amount of 0.2 ml
[2] Time is a period required for recovering the knock-down mudfishes.
[3] Effect is a percentage of the number of recovered mudfishes to that of the dead mudfishes.

What is claimed is:

1. In a process for the preparation of a galenical composition including cut dry leaf or bark of oak tree (*Quercus spp.*) of the type employed as an astringent or mordant in Chinese herb medicine, the improvement comprising uniformly admixing a blend of 70 wt.% of said dry leaf or bark of said oak tree; 20 wt.% of cut dry leaf or root of juniper tree (*Juniperus utilis*); 2.5 wt.% of cut dry root of arrowroot (*Pueraria Thunber giana*); 5 wt.% of cut orange peel containing limonene and nesperidion; and 2.5 wt.% of licorice root (*Glycyrrhiza uralensis*) with water in a weight ratio of 1.3; cooking the first resulting mixture for 5 to 6 hours at a temperature of 40° to 60° C.; extracting the resulting cooked mixture to get a first extract; admixing said first extract with said first mixture in a weight ratio of 3:1; boiling in vacuum the second resulting mixture for 0.5 to 1.0 hour at 110° C. and then extracting said mixture in the presence of water to obtain a second extract; boiling in vacuum said extract for about 4 hours at 110° C. to afford a third extract; and dispersing 0.5 wt.% of glycerin into said extract at 800 to 1000 rpm, and recovering resulting composition useful for counteracting effects of toxic agricultural pesticides.

2. A composition prepared according to the process as claimed in claim 1.

* * * * *